(12) United States Patent
Saitoh et al.

(10) Patent No.: US 8,728,036 B2
(45) Date of Patent: May 20, 2014

(54) ANESTHETIC COMPOUND NEEDLE

(75) Inventors: Hideya Saitoh, Tokyo (JP); Akihiro Saruya, Saitama (JP)

(73) Assignee: Unisis Corporation, Tokyo (JP)

( * ) Notice: Subject to any disclaimer, the term of this patent is extended or adjusted under 35 U.S.C. 154(b) by 143 days.

(21) Appl. No.: 13/144,012

(22) PCT Filed: Mar. 18, 2009

(86) PCT No.: PCT/JP2009/055295
§ 371 (c)(1),
(2), (4) Date: Jul. 11, 2011

(87) PCT Pub. No.: WO2010/106650
PCT Pub. Date: Sep. 23, 2010

(65) Prior Publication Data
US 2011/0276014 A1    Nov. 10, 2011

(51) Int. Cl.
*A61M 5/178*    (2006.01)
(52) U.S. Cl.
USPC .......... 604/165.02; 604/165.01; 604/164.01; 604/164.07
(58) Field of Classification Search
USPC ............ 604/165.01, 165.02, 164.01, 164.06, 604/16.07, 164.12, 264, 272, 117
See application file for complete search history.

(56) References Cited

U.S. PATENT DOCUMENTS

| | | | |
|---|---|---|---|
| 5,135,505 A * | 8/1992 | Kaufman | 604/165.02 |
| 5,320,608 A | 6/1994 | Gerrone | |
| 5,456,673 A * | 10/1995 | Ziegler et al. | 604/264 |
| 5,480,389 A * | 1/1996 | McWha et al. | 604/165.02 |

(Continued)

FOREIGN PATENT DOCUMENTS

| | | |
|---|---|---|
| JP | 6-44549 | 6/1994 |
| JP | 10-305101 | 11/1998 |

(Continued)

OTHER PUBLICATIONS

Supplementary European Search Report issued Apr. 19, 2012 in European Patent Application No. EP 09 84 1855.

(Continued)

*Primary Examiner* — Bhisma Mehta
*Assistant Examiner* — Laura Schell
(74) *Attorney, Agent, or Firm* — Wenderoth, Lind & Ponack, L.L.P.

(57) ABSTRACT

A front portion of a tubular inner needle proximal end portion disposed at a proximal end of the inner needle is attached to a rear end portion of a tubular adaptor, a tubular outer needle proximal end portion disposed at a proximal end of the outer needle is inserted from a distal end of the adaptor, and a distal end of the inner needle is caused to protrude from a distal end of the outer needle. A restricting plate having an insertion hole through which the outer needle proximal end portion is inserted is inserted into the adaptor from an opening formed in an upper surface of the adaptor. A protrusion formed on a lower surface of the insertion hole protrudes upward and engages with one of the grooves of the outer needle proximal end portion. When the restricting plate is pushed down, the groove of the outer needle proximal end portion and the protrusion of the restricting plate are disengaged from each other and the inner needle is set to the unlocked state in which the inner needle is able to be advanced or retracted relative to the outer needle.

6 Claims, 12 Drawing Sheets

(56) References Cited

U.S. PATENT DOCUMENTS

| | | |
|---|---|---|
| 5,836,914 A | 11/1998 | Houghton |
| 5,871,470 A | 2/1999 | McWha |
| 2001/0053918 A1 | 12/2001 | Ouchi |
| 2004/0116954 A1 | 6/2004 | Pagliuca et al. |
| 2006/0155246 A1 | 7/2006 | Higuchi et al. |
| 2007/0270640 A1* | 11/2007 | Dimitriou et al. ............ 600/106 |

FOREIGN PATENT DOCUMENTS

| | | |
|---|---|---|
| JP | 2943856 | 6/1999 |
| JP | 2001-353219 | 12/2001 |
| JP | 2002-306596 | 10/2002 |
| JP | 2003-199828 | 7/2003 |
| WO | 2004-091702 | 10/2004 |
| WO | 2004/091702 | 10/2004 |

OTHER PUBLICATIONS

International Search Report mailed Apr. 14, 2009 in International (PCT) Application No. PCT/JP2009/055295.

Written Opinion of the International Searching Authority issued Apr. 2, 2009 in International (PCT) Application No. PCT/JP2009/055295.

* cited by examiner

ANESTHETIC COMPOUND NEEDLE

TECHNICAL FIELD

This application is a national phase application based on PCT/JP2009/055295, filed Mar. 18, 2009. The present invention relates to an anesthetic compound needle for administering epidural anesthesia or spinal anesthesia.

BACKGROUND ART

As an anesthetic needle used to administer spinal anesthesia, a compound needle including outer and inner needles as disclosed in Patent Document 1 below (Japanese Unexamined Utility Model Registration Application Publication No. 6-44549) is known. With this compound needle, the outer needle is inserted in order to cause a distal end thereof to reach the epidural space. After that, the inner needle is inserted into the outer needle so as to cause a distal end thereof to protrude from the distal end of the outer needle, to penetrate through the dura mater, and to reach the subarachnoidal space. Then, spinal anesthesia is administered by injecting an anesthetic solution through the inner needle into the subarachnoidal space. In this spinal anesthesia, during a confirming operation after the inner needle has penetrated through the dura mater or during a medicine injecting operation, the inner needle may be advanced or retracted. This may cause the distal end of the inner needle to move out of the dura mater and result in failure of spinal anesthesia, or may cause the distal end of the inner needle to be excessively inserted and damage nerve tissue. For this reason, it is desirable that the inner needle can be fixed so as not to be advanced or retracted relative to the outer needle. Patent Document 2 below (Japanese Unexamined Patent Application Publication No. 10-305101) discloses a compound needle, an inner needle of which can be fixed as described above. In this compound needle, a base portion of a proximal end of an outer needle and a proximal end portion of a proximal end of an inner needle are threadably engaged with each other. The inner needle, when rotated, can be advanced or retracted relative to the outer needle, and when not rotated, fixed relative to the outer needle.

Although a mechanism disclosed in Patent Document 2 above in which the proximal end portions of the inner and outer needles are threadably engaged with each other can fix the inner needle relative to the outer needle, the inner needle needs to be rotated in order to be advanced or retracted. Thus, operation is very complex. In addition, there is a significant disadvantage that insertion of the inner needle into the dura mater cannot be sensed.

Patent Document 3 below (Japanese Unexamined Patent Application Publication No. 2002-306596) discloses a technology that overcomes the above-described problems. With this technology, by rotating an inner needle by 180° or a smaller angle relative to an outer needle, an unlocked state, in which the inner needle can be advanced or retracted relative to the outer needle, and a locked state, in which the inner needle cannot be advanced or retracted relative to the outer needle, can be switched. In the unlocked state, the inner needle can be straightly advanced relative to the outer needle without resistance. Thus, a moment when the distal end of the inner needle is inserted into the dura mater can be clearly sensed.

Patent Document 1: Japanese Unexamined Utility Model Registration Application Publication No. 6-44549
Patent Document 2: Japanese Unexamined Patent Application Publication No. 10-305101
Patent Document 3: Japanese Unexamined Patent Application Publication No. 2002-306596

With the technology disclosed in Patent Document 3 above, the amount of rotation of the inner needle can be markedly reduced compared to that in the technology disclosed in Patent Document 2 above, and accordingly, can cause the moment when the distal end of the inner needle is inserted into the dura mater to be clearly sensed due to insertion resistance. However, the locked and unlocked states are switched by rotating the inner needle. Some anesthesiologists suggest that it is unavoidable that the internal needle, when it is rotated, is slightly advanced or retracted. Thus, the anesthesiologists need to pay close attention while administering anesthesia. Still, in many cases, there is a possibility of damaging nerve tissue due to advancement of the inner needle and a possibility of failure of spinal anesthesia caused by removal of the distal end of the inner needle from the dura mater due to retraction of the inner needle.

An object of the present invention is to develop an anesthetic compound needle that allows an unlocked state, in which the inner needle can be advanced or retracted relative to the outer needle, and a locked state, in which the inner needle cannot be advanced or retracted relative to the outer needle, to be switched by a simple operation without rotating the inner needle. This arrangement allows the moment when the distal end of the inner needle is inserted into the dura mater to be clearly sensed.

SUMMARY OF THE INVENTION

According to the present invention, an anesthetic compound needle includes an outer needle, an inner needle, and a tubular adaptor. A front portion of a tubular inner needle proximal end portion disposed at a proximal end of the inner needle is attached to a rear end portion of the adaptor. A tubular outer needle proximal end portion disposed at a proximal end of the outer needle is inserted from a distal end of the adaptor, and a distal end of the inner needle is caused to protrude from a distal end of the outer needle.

A plurality of grooves are formed in parallel in a peripheral direction along an axial direction of the outer needle proximal end portion at least in a lower surface of the outer needle proximal end portion.

A restricting plate having an insertion hole through which the outer needle proximal end portion is inserted is inserted into the adaptor from an opening formed in an upper surface of the adaptor. The adaptor is provided with an urging means that urges the restricting plate upward when the restricting plate is pushed downward and that pushes the restricting plate upward when the pushing-down force is released.

A protrusion protrudes upward and engages with one of the grooves of the outer needle proximal end portion is formed on a lower surface of the insertion hole of the restricting plate.

When the restricting plate is pushed down, the groove of the outer needle proximal end portion and the protrusion of the restricting plate are disengaged from each other and the inner needle is set to an unlocked state in which the inner needle is able to be advanced or retracted relative to the outer needle. When the pushing down is released, the restricting plate moves up and one of the grooves of the outer needle proximal end portion and the protrusion of the restricting plate are engaged with each other and the inner needle is set to a locked state in which the inner needle is unable to be advanced or retracted relative to the outer needle.

Since the present invention has the above-described structure, with a simple operation of pushing down the restricting plate, the groove of an insertion portion and the protrusion of the restricting plate are disengaged from each other and the inner needle is set to the unlocked state in which the inner needle is able to be advanced or retracted relative to the outer needle. Thus, the inner needle can be advanced and the moment when the distal end of the inner needle is inserted into the dura mater can be clearly sensed. When the pushing down of the restricting plate is released (finger is removed from the restricting plate), the restricting plate automatically moves up due to the operation of the urging means. One of the grooves of the insertion portion and the protrusion of the restricting plate are engaged with each other, and the inner needle is set to the locked state in which the inner needle is unable to be advanced or retracted relative to the outer needle. Thus, there is no possibility of the inner needle moving relative to the outer needle when an anesthetic solution is injected through the inner needle into the subarachnoidal space, and spinal anesthesia can be safely administered.

According to the present invention, the urging means may be a plate spring portion defined by forming a cutout portion in a lower surface of the adaptor.

The urging means according to the present invention is not particularly limited to a specific component. The urging means may include a highly elastic material such as a plate spring formed as a separate member, a coil spring, or rubber attached to a lower portion of the adaptor. However, by defining the plate spring portion by forming the cutout in the lower surface of the adaptor, that is, by forming the cutout portion around the plate spring portion except part of it, the plate spring portion can be used as the urging means due to elasticity of a material (plastic, metal, or the like) of the adaptor without providing the urging means of the separate member. Thus, due to the reduced number of assembly members, assembly work and cost can be reduced, and the size of the adaptor can also be made as small as possible.

According to the present invention, a finger contact portion bent in a horizontal direction may be formed in an upper portion of the restricting plate.

By forming the finger contact portion, a finger can be placed on the finger contact portion when restricting plate is pushed down. Thus, an area with which the finger is in contact is increased, and accordingly, the operation can be easily and reliably performed.

ADVANTAGES

In the anesthetic compound needle according to the present invention, the locked and unlocked states of the inner needle can be switched by a simple operation of pushing down of the restricting plate or by releasing the pushing down of the restricting plate without rotating the inner needle. Thus, there is no possibility of the inner needle being casually advanced or retracted when the state of the inner needle is switched, and accordingly, an anesthesia procedure can be safely performed.

Figure 1:
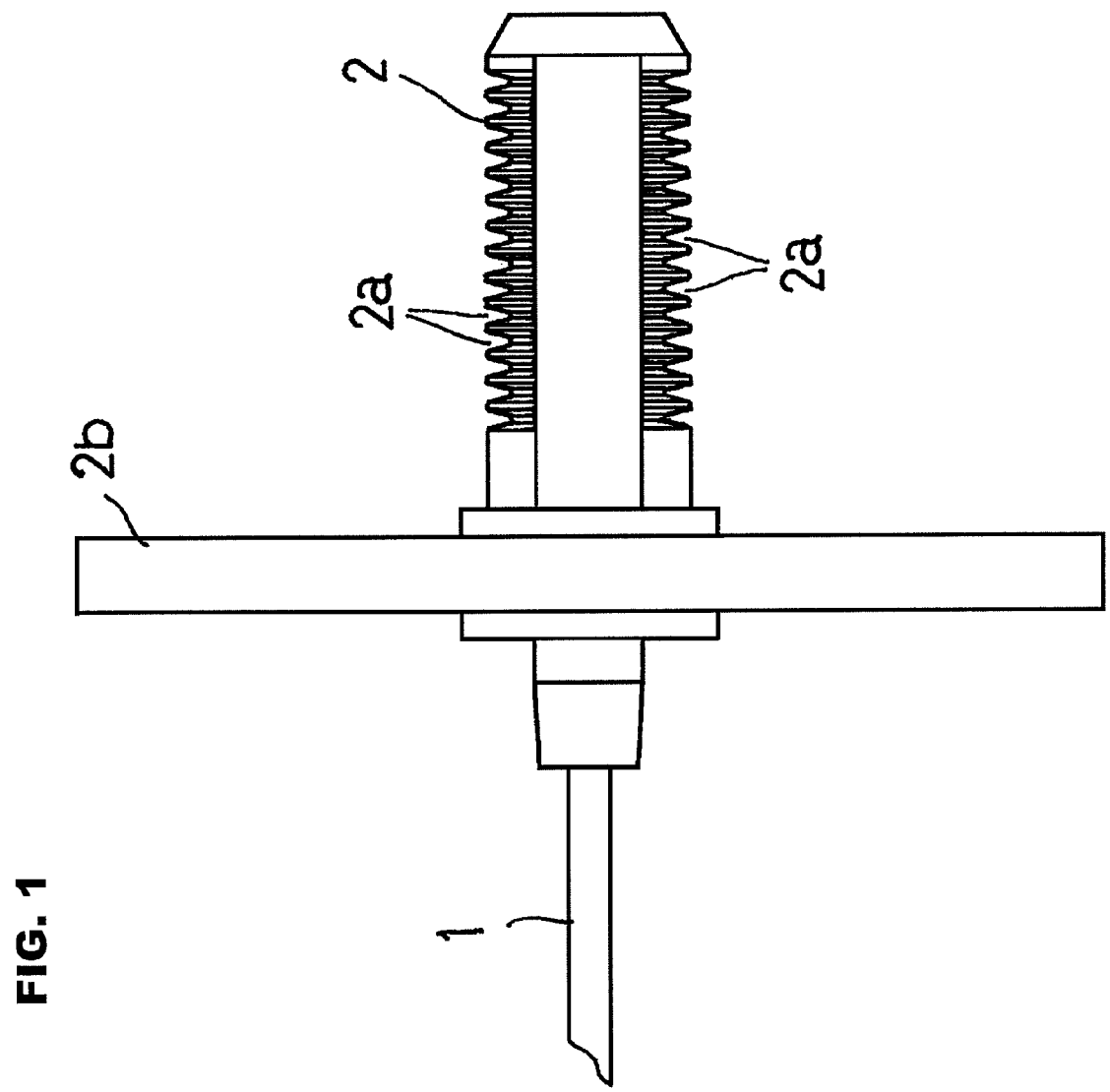
FIG. 1 is a side view of an outer needle proximal end portion.

REFERENCE NUMERALS 1 outer needle
1b distal end bent portion
1c through hole
1d blade edge hole
2 outer needle proximal end portion
2a groove
2b blade
3 inner needle
4 inner needle proximal end portion
4a insert portion
4b peripheral groove
4c medicine receiving portion
5 adaptor
5a opening
5b cutout portion
5c plate spring portion
5d annular rib
6 restricting plate
6a insertion hole
6b protrusion
6c finger contact portion
9 catheter
10 subarachnoidal space
11 dura mater
12 epidural space
13 yellow ligament

DETAILED DESCRIPTION OF THE INVENTION

Embodiment

The present invention will be described in detail below with reference to the drawings relating to an embodiment.

A compound needle according to the present invention includes an inner needle and an outer needle.

Figure 2:
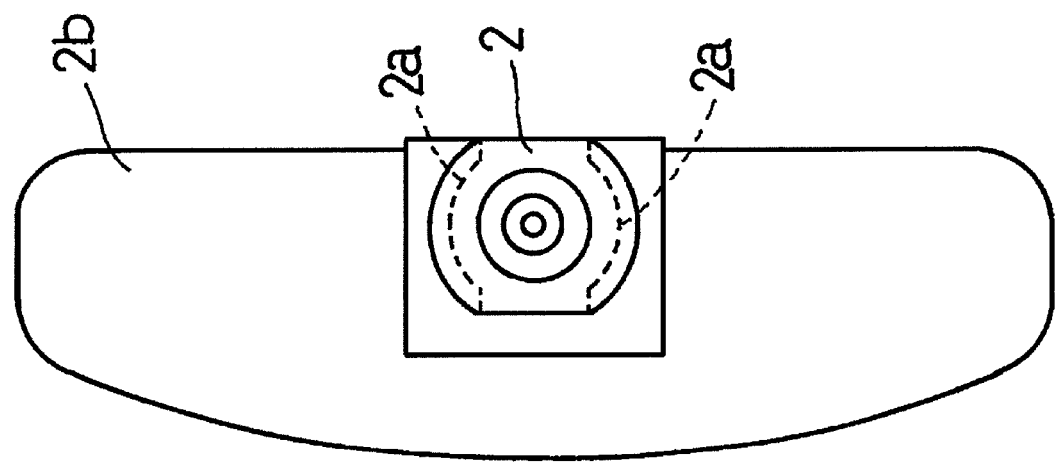
FIG. 2 is a rear view of the outer needle proximal end portion.

As illustrated in FIGS. 1 and 2, a tubular outer needle proximal end portion 2 (formed of plastic) is disposed at a proximal end of an outer needle 1. A number of grooves 2a are formed in parallel in an upper surface in a peripheral direction and a lower surface of the outer needle proximal end portion 2 along the axial direction of the outer needle proximal end portion 2. It is sufficient that the grooves in the peripheral direction are formed at least in the lower surface of the outer needle proximal end portion. However, if the grooves are also formed in the upper surface as in the present embodiment, the outer needle or the inner needle can be used even when the needle is vertically inverted. The grooves in the peripheral direction may also be formed around the whole periphery of the outer needle proximal end portion.

The outer needle proximal end portion 2 also includes a blade 2b mounted therein, which assists in inserting the outer needle and in switching between unlocked and locked states of the inner needle.

Figure 11:
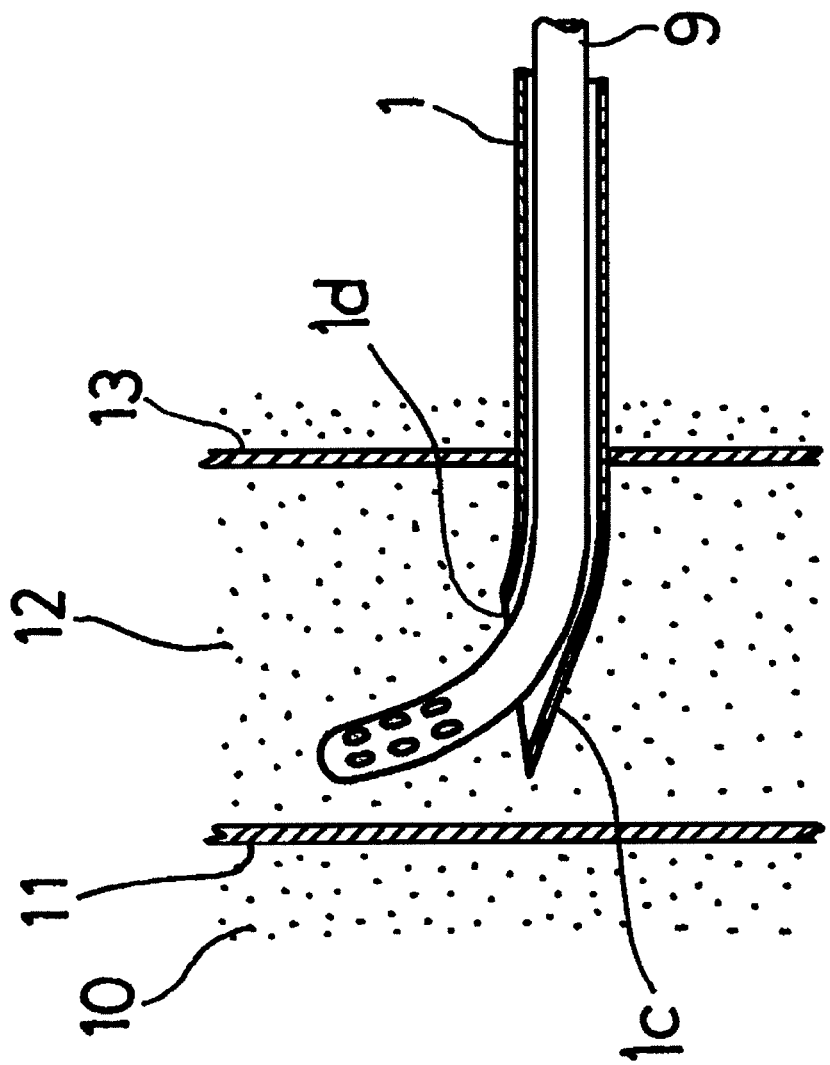
FIG. 11 is an explanatory view illustrating how an anesthetic compound needle according to an embodiment is used.
Figure 12:
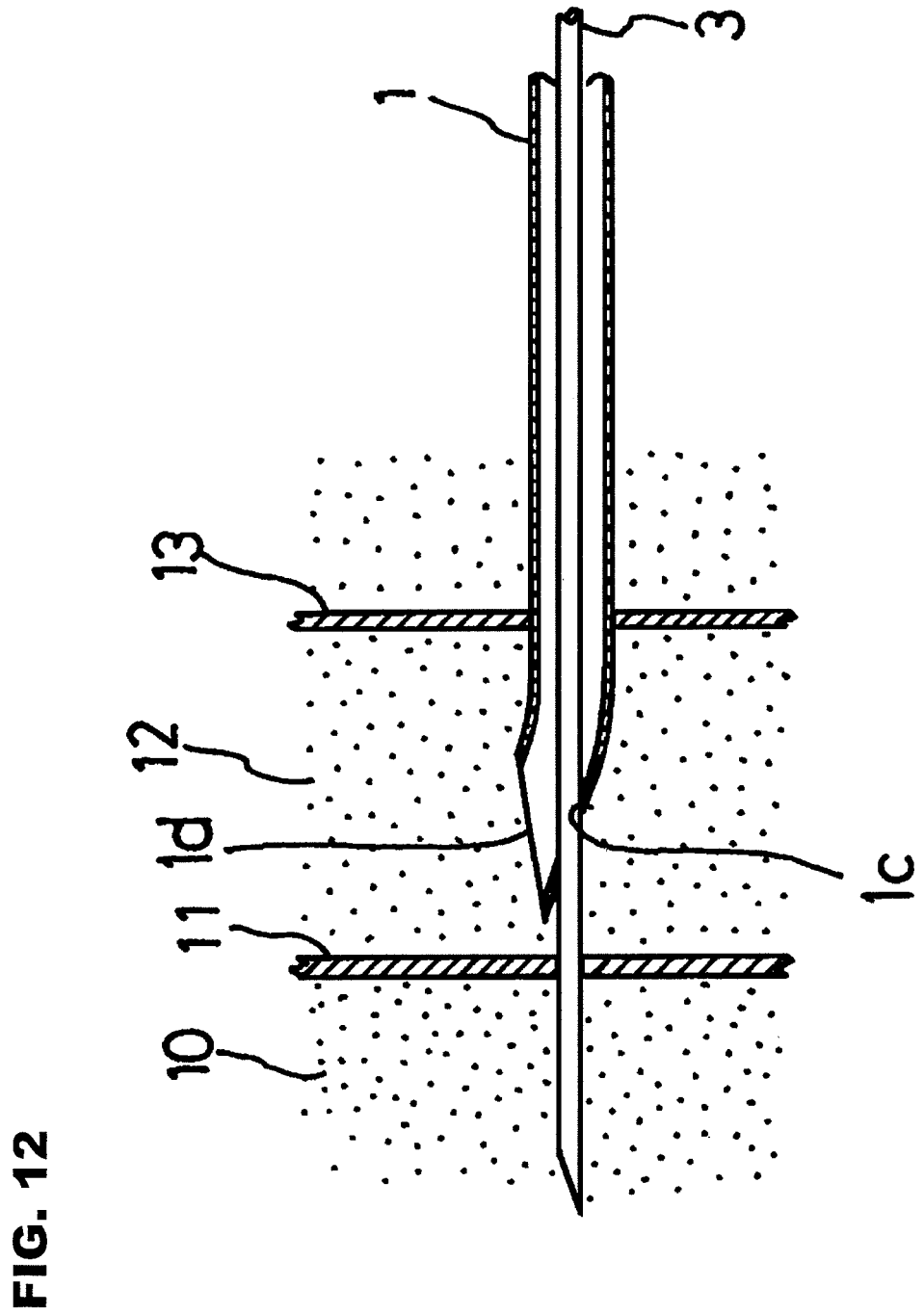
FIG. 12 is an explanatory view illustrating how the anesthetic compound needle according to the embodiment is used.

As illustrated in FIGS. 11 and 12, a distal end of the outer needle 1 includes a distal end bent portion 1b, which is bent upward in an elbow-like shape. The distal end bent portion 1b has a through hole 1c, from which a distal end of an inner needle 3 protrudes. The distal end bent portion 1b also has a blade edge hole 1d from which a distal end of a catheter protrudes.

The outer needle 1 is inserted into a body with an outer needle stylet (not shown) inserted thereinto from the rear of the outer needle proximal end portion 2 while the through hole 1c and the blade edge hole 1d are substantially blocked. This is the same as with a related art compound needle. The purpose of this is the prevention of damage to skin tissue or the like of a patient by the outer through hole 1c and the blade edge hole 1d. After the outer needle has been inserted, the outer needle stylet is removed from the outer needle. A plastic proximal end portion is provided at a proximal end of the outer needle stylet so as to cause the proximal end portion of the outer needle stylet to be engaged with a rear end portion of the outer needle proximal end portion 2 when the outer needle stylet has been inserted through the outer needle 1.

Figure 3:
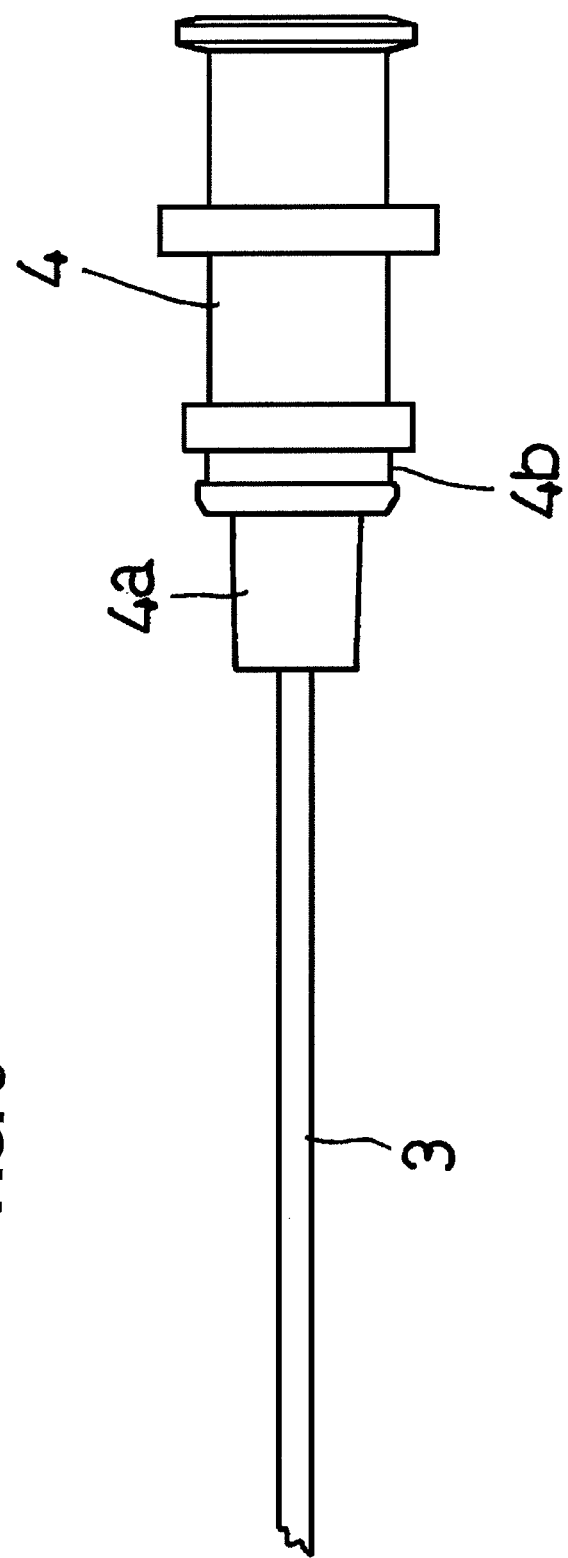
FIG. 3 is a plan view of an inner needle proximal end portion.
Figure 9:
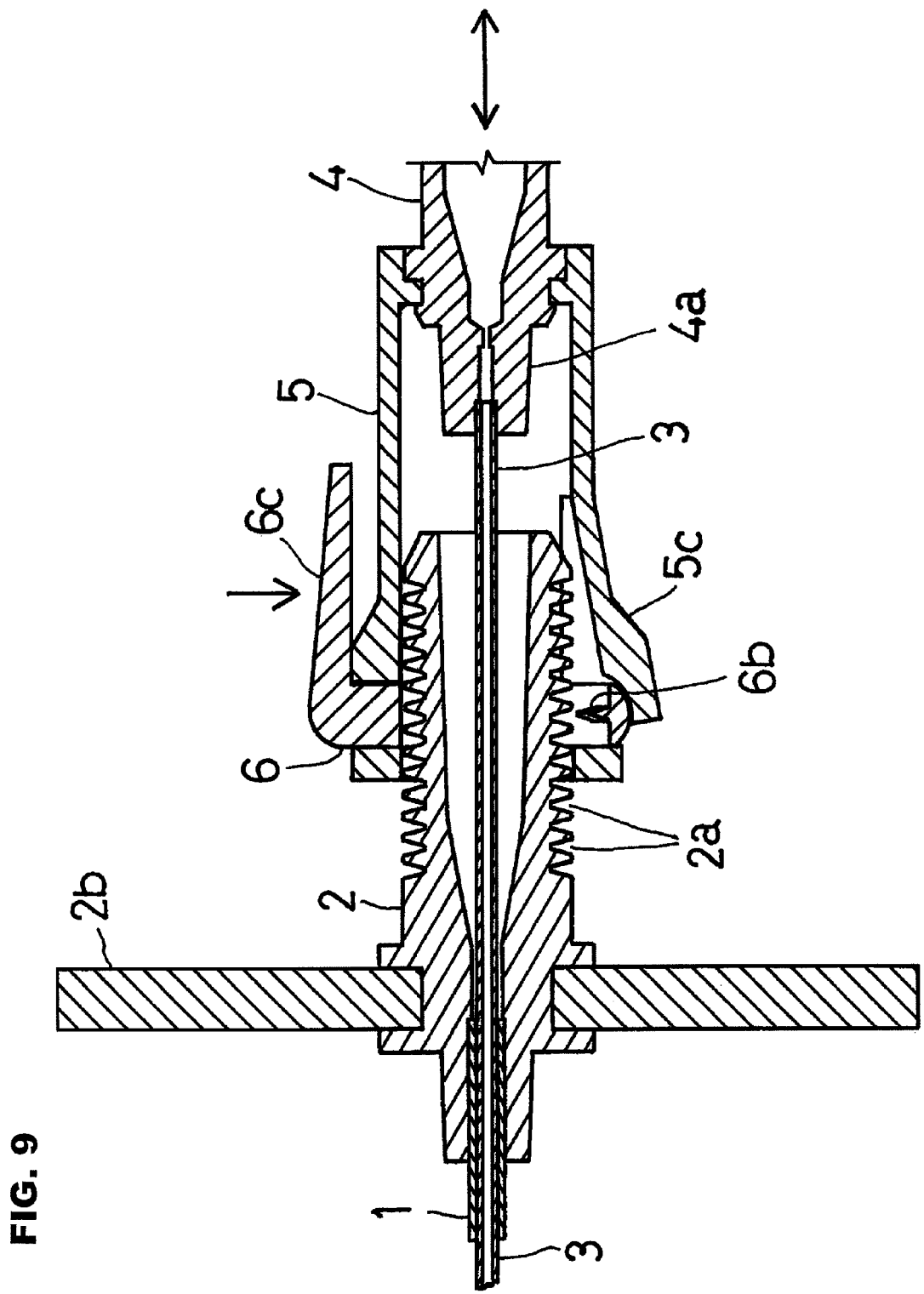
FIG. 9 is a sectional explanatory view of a compound needle of which the inner needle is set to an unlocked state relative to the outer needle.
Figure 10:
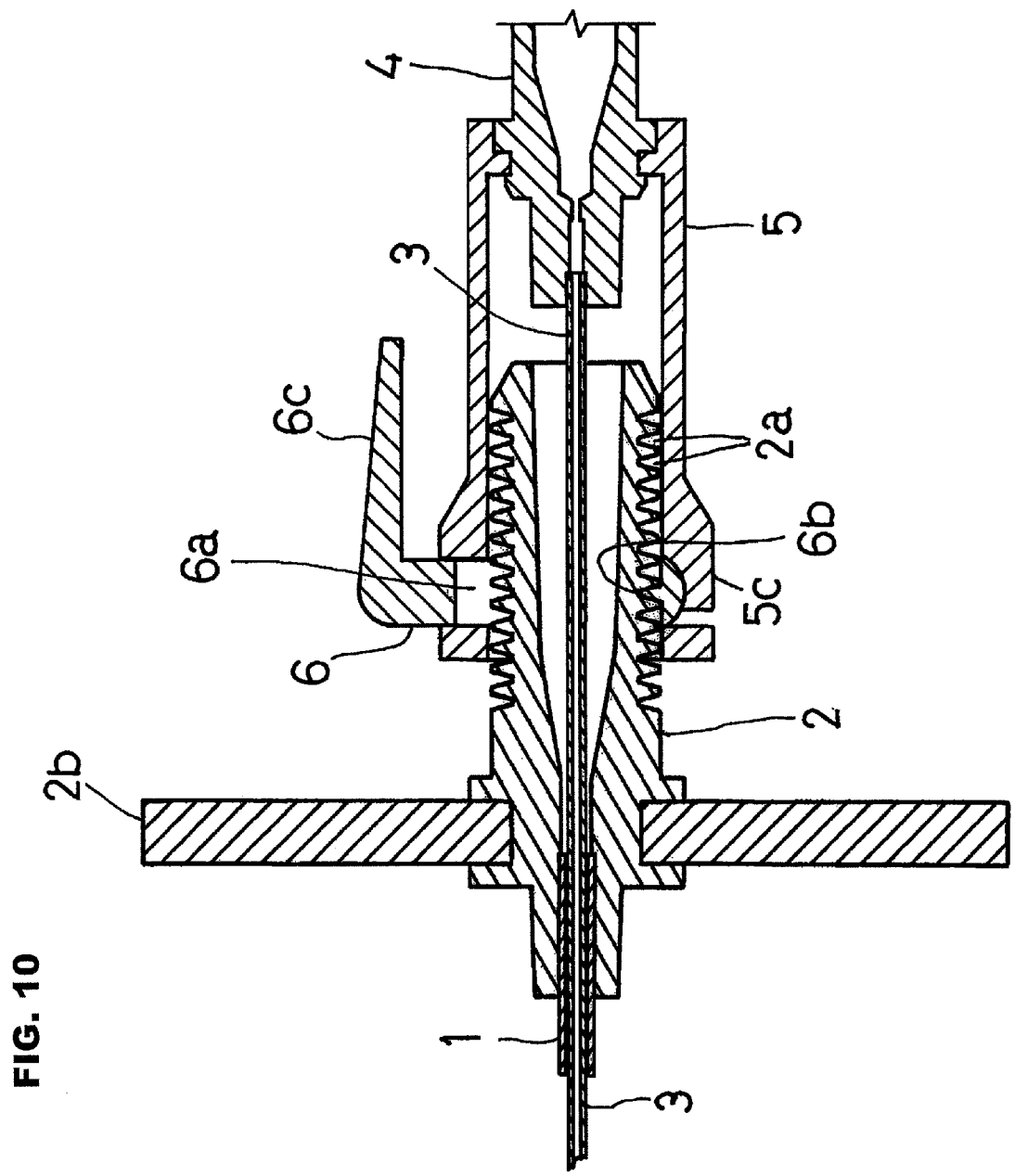
FIG. 10 is a sectional explanatory view of the compound needle of which the inner needle is set to a locked state relative to the outer needle.

As illustrated in FIGS. 9 and 10, the inner needle 3 is inserted into the outer needle 1, the distal end of which protrudes from the through hole 1c at the distal end of the outer needle 1 (FIG. 11). A tubular inner needle proximal end portion 4 (formed of plastic) is disposed at a proximal end of the inner needle 3. The inner needle proximal end portion 4 includes a tubular insert portion 4a at a front portion thereof. A peripheral groove 4b (see FIG. 3), which is engaged with an adaptor, is formed around the insert portion. A medicine receiving portion 4c used to receive a medicine is formed at a rear end of the inner needle proximal end portion 4.

As is the case with a related art compound needle, an inner needle stylet (not shown) is inserted into the inner needle when the inner needle 3 is inserted into the outer needle 1. When the inner needle stylet has been inserted, the position of a distal end of the stylet substantially matches the position of the distal end of the inner needle. Thus, a blade edge hole of the inner needle is substantially blocked. The purpose of this is the prevention of damage to tissues such as dura mater when the inner needle 3 is caused to protrude from the through hole at the distal end of the outer needle 1. A plastic proximal end portion is provided at a proximal end of the inner needle stylet so as to cause the proximal end portion of the stylet to be engaged with the rear end portion of the inner needle proximal end portion 4 when the inner needle stylet has been inserted through the inner needle 3.

Figure 4:
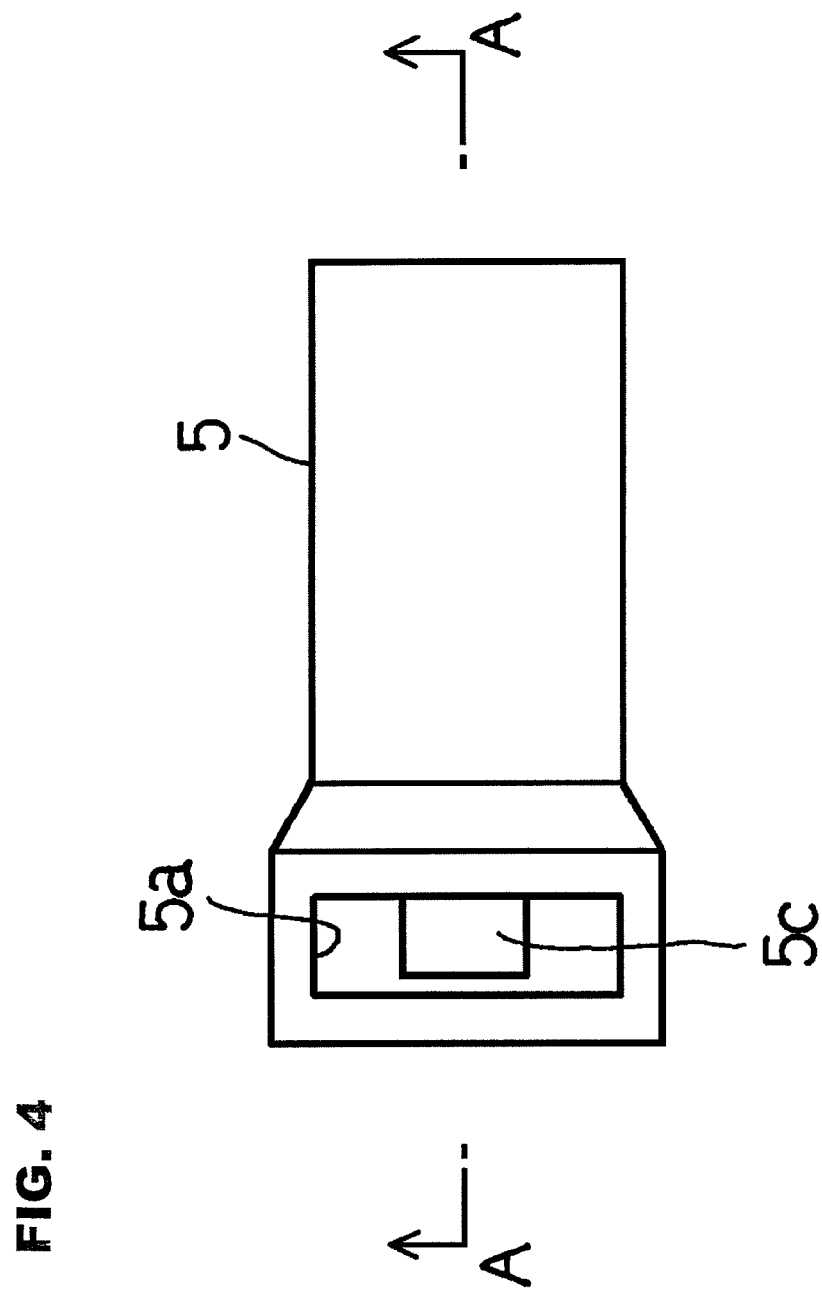
FIG. 4 is a plan view of an adaptor.
Figure 5:
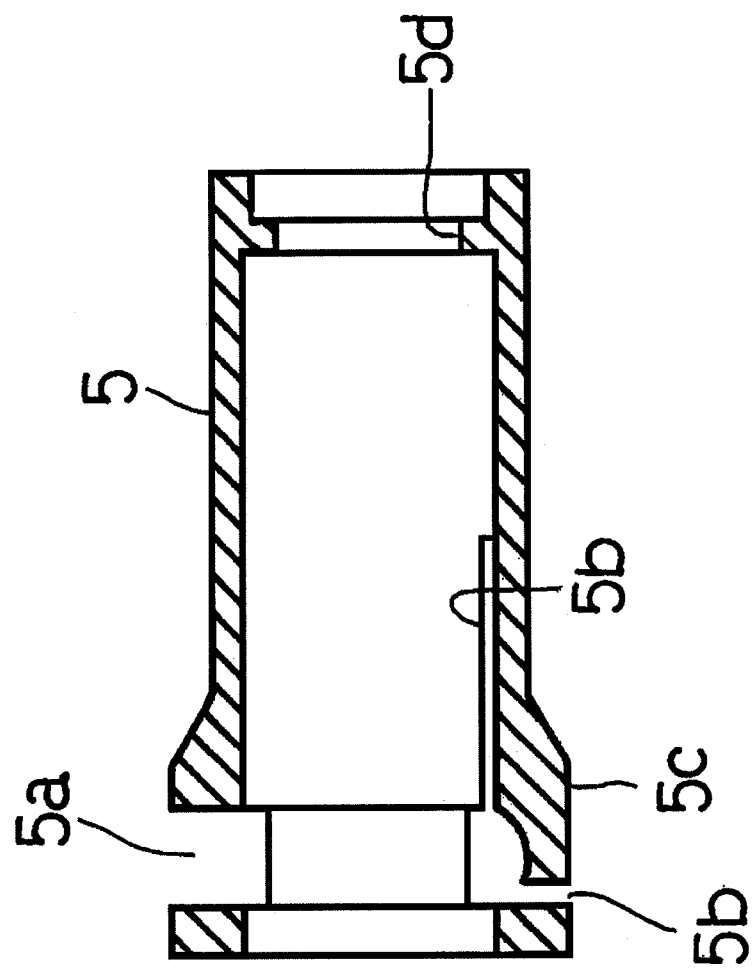
FIG. 5 is a sectional view of the adaptor illustrated in FIG. 4 taken along line A-A.
Figure 6:
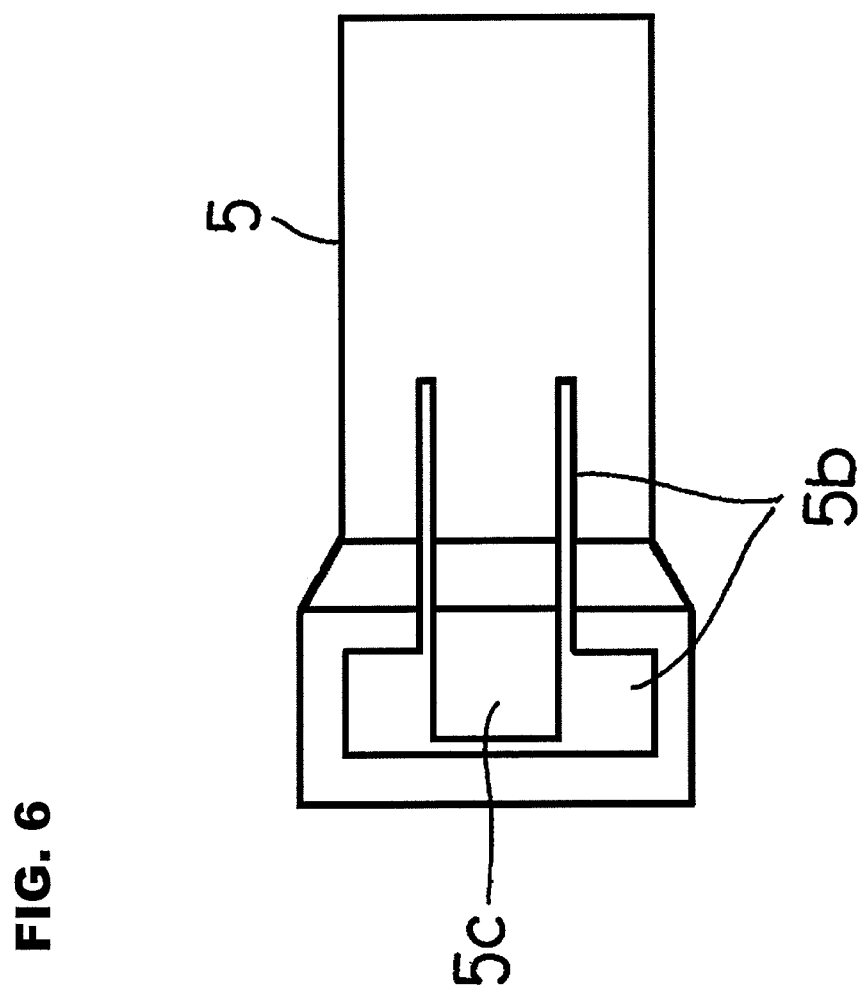
FIG. 6 is a bottom view of the adaptor.

As illustrated in FIGS. 4 to 6, an adaptor 5 is formed of plastic and has a tubular shape. The outer needle proximal end portion 2 is inserted into the adaptor 5 from a front end side, and the insert portion 4a of the inner needle proximal end portion 4 is inserted into the adaptor 5 from a rear end side. An annular rib 5d is formed around an inner peripheral surface at the rear end side of the adaptor 5 so as to be engaged with the inner needle proximal end portion.

An opening 5a is formed in an upper surface of the adaptor 5, through which a restricting plate 6 is inserted. In a lower surface of the adaptor 5, a plate spring portion 5c is formed, which is defined by a cutout portion 5b. The plate spring portion 5c has a rectangular shape and functions as a plate spring because of the formation of the cutout portion 5b around the plate spring portion 5c except part of it (a side on the right in FIG. 6). As illustrated in FIG. 6, part of the cutout portion 5b is larger than the remaining part thereof in order to prevent the cutout portion 5b from interfering with the restricting plate 6 when the plate is pushed down. A large cutout portion such as this may not be required. For example, such a large cutout portion is unnecessary if the bottom of the adaptor is deeper in that portion.

Figure 7:
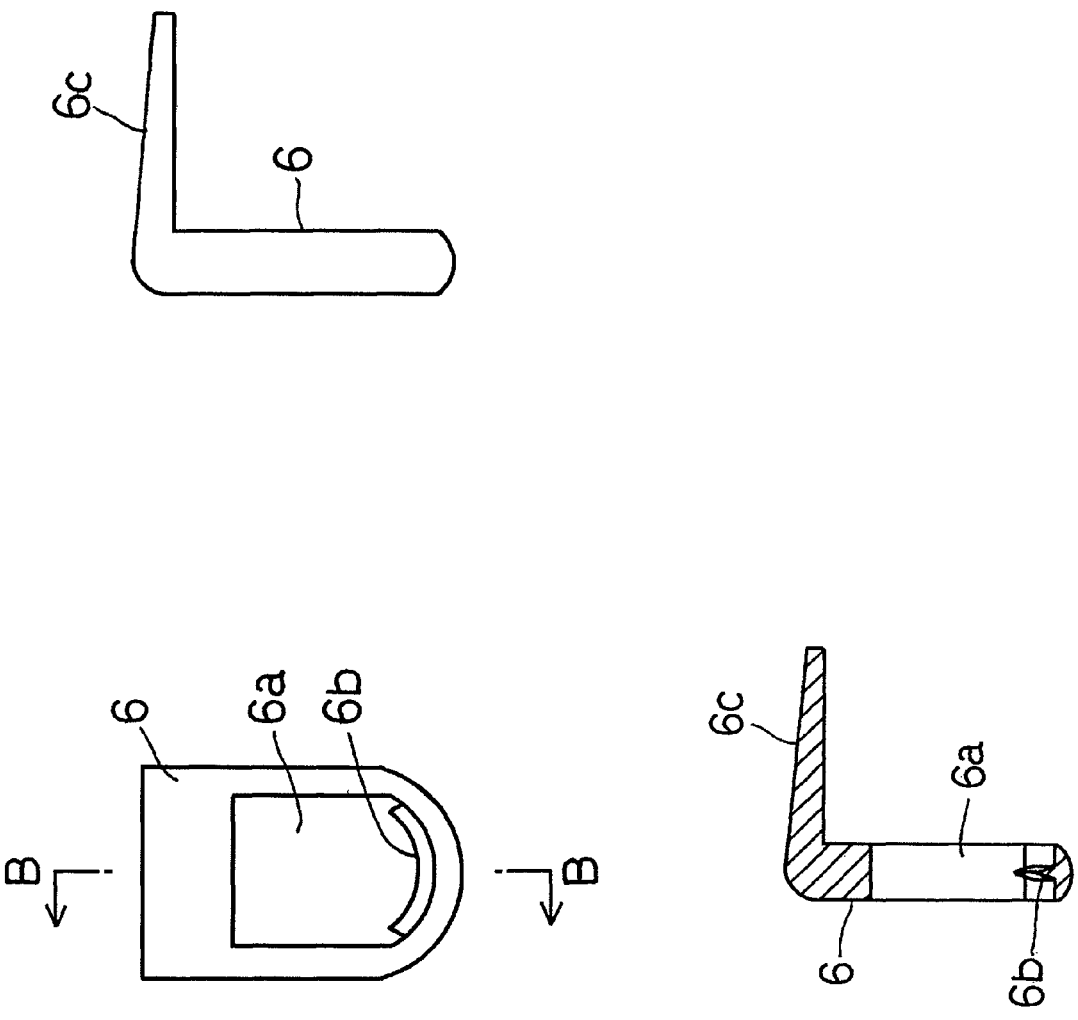
FIG. 7 includes front and side views of a restricting plate, and a sectional view of the restricting plate taken along line B-B.

FIG. 7 relates to the restricting plate 6, illustrating a front view on the upper left, a side view on the upper right, and a sectional view taken along line B-B on the lower left. The restricting plate is formed to have a plate-like shape, an upper portion of which is bent at substantially right angle into a horizontal direction so as to define a finger contact portion 6c, and of which a lower portion has a circular arc shape that matches the inner peripheral shape of the adaptor 5. An insertion hole 6a is formed through the restricting plate in the axial direction in order for the outer needle proximal end portion 2 to be inserted therethrough. The horizontal width of the insertion hole 6a is equal to or a little larger than the horizontal width of the outer needle proximal end portion 2. The vertical width of the insertion hole 6a is larger than the vertical width of the outer needle proximal end portion 2 so as not to obstruct pushing down of the restricting plate. A protrusion 6b is formed on a lower surface of the insertion hole 6a and protrudes upward. The section of the protrusion 6b has a U-shape similar to that of each groove 2a of the outer needle proximal end portion 2.

Figure 8:
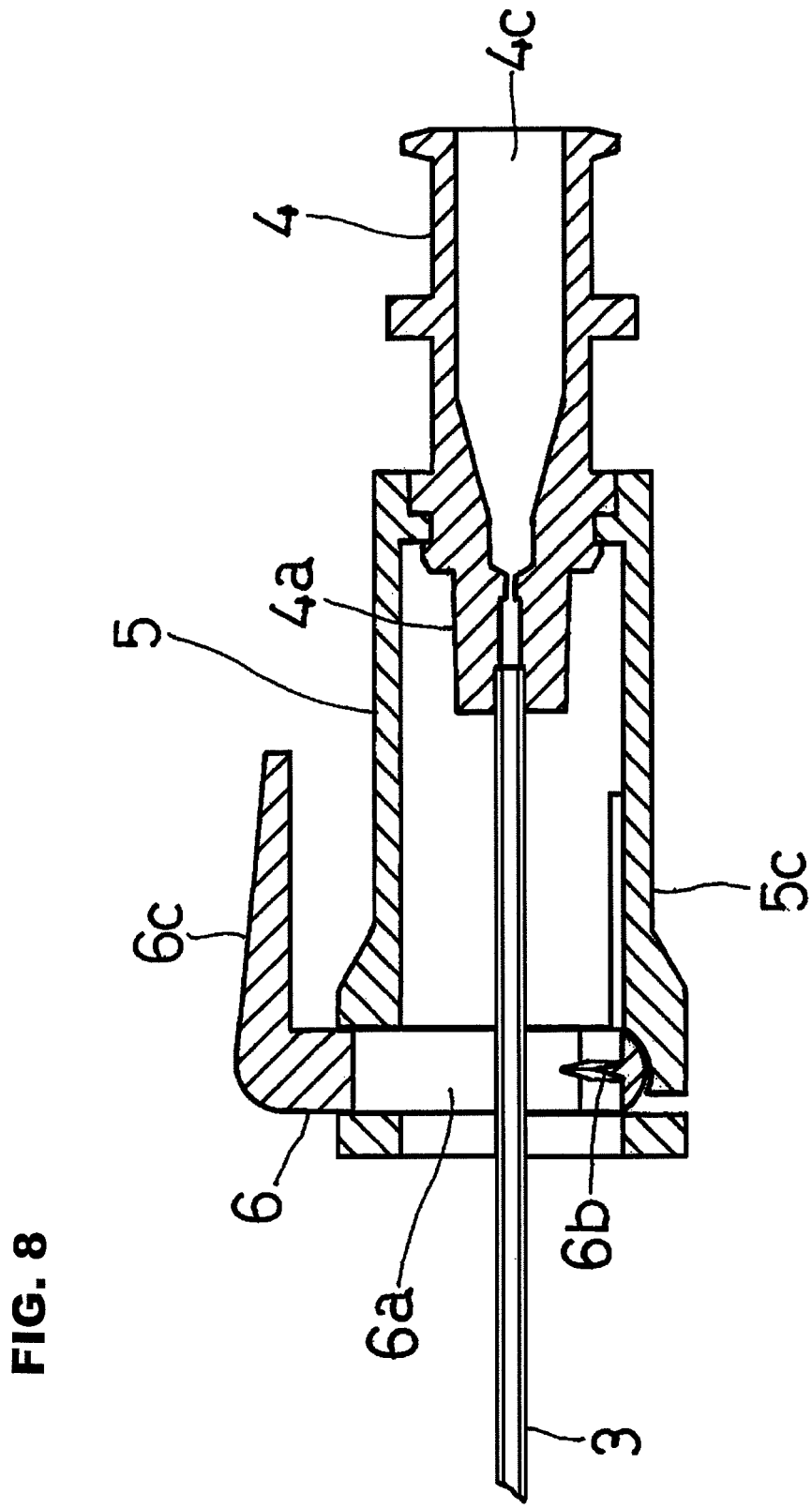
FIG. 8 is a longitudinal sectional view of a state in which the inner needle proximal end portion is engaged with the adaptor.

After the restricting plate 6 is inserted into the adaptor 5 through the opening 5a, as illustrated in FIG. 8, the inner needle proximal end portion 4 is attached to the adaptor 5 by inserting the insert portion 4a from the rear end side of the adaptor 5 such that the peripheral groove 4b is engaged with the annular rib 5d. Thus, the adaptor 5 and the inner needle proximal end portion 4 are integrated into a unit. In this state, the restricting plate 6 does not fall off the adaptor 5 because of the inner needle 3 being inserted through the insertion hole 6a.

The method of attaching the front portion of the inner needle proximal end portion 4 to the rear end portion of the adaptor 5 is not limited to the engagement as illustrated in the present embodiment. Any method including adhesion with adhesive or welding of a plastic material may be used.

In order to insert the inner needle 3 into the outer needle 1, as illustrated in FIG. 9, a finger is placed on the finger contact portion 6c so as to push down the restricting plate 6. In this state, the outer needle proximal end portion 2 is inserted into the adaptor 5. At this time, the plate spring portion 5c of adaptor 5 is pushed down by the restricting plate 6 and elastically deformed, and the protrusion 6b is not engaged with any of the grooves 2a of the outer needle proximal end portion 2. Thus, the inner needle 3 can be freely advanced or retracted with respect to the outer needle 1 (unlocked state).

As illustrated in FIG. 10, the finger is removed from the finger contact portion 6c when the inner needle 3 reaches an appropriate position (releasing of pushing down). This causes the plate spring portion 5c to return to its original position due to the elasticity thereof, thereby pushing up the restricting plate 6 and causing the protrusion 6b to be engaged with one of the grooves 2a. Thus, the inner needle cannot be advanced or retracted relative to the outer needle (locked state).

An anesthetic compound needle according to the present embodiment is used as follows. That is, the outer needle 1 is inserted into a patient with the outer needle stylet (not shown) inserted therethrough, and the distal end of the outer needle 1 is caused to reach an epidural space 12. The outer needle stylet is removed while keeping the outer needle 1 at the position it has reached. Next, the inner needle 3 (engaged with the adaptor) is inserted into the outer needle with the inner needle stylet inserted therethrough. As the outer needle proximal end portion 2 passes into the adaptor 5, the restricting plate 6 is pushed down by a finger placed on the finger contact portion 6c. In this state, the inner needle 3 is advanced into outer needle 1.

The distal end of the inner needle 3 is caused to protrude from the through hole at the distal end of the outer needle 1, to penetrate through the dura mater 11, and to reach a subarachnoidal space 10 as illustrated in FIG. 11. Since the state at this time is, as illustrated in FIG. 9, the unlocked state in which the protrusion 6b is not engaged with any of the grooves 2a, the adaptor 5 (and inner needle 3) can be straightly advanced or retracted without resistance relative to the outer needle proximal end portion 2 (that is, the inner needle 3 relative to the outer needle 1). Thus, a moment when the distal end of the inner needle is inserted into the dura mater can be clearly sensed, and accordingly, the percentage of success in spinal anesthesia is increased.

Then, the finger is removed from the finger contact portion 6c (releasing of pushing down) so as to set the inner needle to the locked state in which the inner needle cannot be advanced or retracted relative to the outer needle, the inner needle stylet is removed while keeping the outer needle 1 and the inner needle 3 at the positions they have reached, a medicine injecting device such as an injector is connected to the medicine receiving portion 4c of the inner needle proximal end portion 4, and spinal anesthesia is administered by injecting an anesthetic solution from the distal end of the inner needle 3 into the subarachnoidal space 10 (FIG. 11). Since the inner needle 3 is set to the locked state, the series of above operations can be safely performed. In addition, depending on the case, epidural anesthesia can also be administered after that by performing the following operation. That is, the inner needle 3 is set to the unlocked state by pushing down the finger contact portion 6c (restricting plate 6), the inner needle 3 is removed from the outer needle 1, and a catheter 9 instead of the inner needle 3 is inserted through the outer needle 1. The distal end of the catheter 9 is caused to protrude from the blade edge hole 1d of the outer needle 1, only the outer needle 1 is removed, and the anesthetic solution is injected from the catheter 9 kept in the position it has reached into the epidural space 12 (FIG. 12).

Spinal anesthesia has a strong and immediate effect but does not last long. Epidural anesthesia has a weaker effect but lasts longer compared to spinal anesthesia. With a combined use of spinal anesthesia and epidural anesthesia, anesthesia can be administered in a more ideal manner.

The invention claimed is:

1. An anesthetic compound needle comprising:
an outer needle;
an inner needle;
a tubular adaptor;
a tubular inner needle proximal end portion at a proximal end of said inner needle and having a front portion attached to a rear end portion of said adaptor;
a tubular outer needle proximal end portion at a proximal end of said outer needle and inserted through an opening in a distal end of said adaptor, and a distal end of said inner needle protruding from a distal end of said outer needle;
a plurality of parallel peripherally-extending grooves formed along an axial direction on a lower outer surface of said outer needle proximal end portion; and
a restricting plate having an insertion hole through which said outer needle proximal end portion is inserted, said restricting plate being inserted into said adaptor through an opening in an upper surface of said adaptor, said adaptor having a plate spring portion for urging said restricting plate upward when said restricting plate is pushed downward and for pushing said restricting plate upward when the downward pushing force is released, said plate spring portion being formed of a cutout portion in a lower surface of said adaptor;
wherein said restricting plate has a protrusion formed on a lower surface of said insertion hole, said protrusion protruding upward so as to engage one of said grooves on said lower outer surface of said outer needle proximal end portion;
wherein said adaptor, said outer needle proximal end portion, and said restricting plate are configured so that, when said restricting plate is pushed downward, said grooves on said outer needle proximal end portion and said protrusion of said restricting plate are disengaged from each other so that said inner needle is in an unlocked state to allow said inner needle to be advanced or retracted relative to said outer needle; and
wherein said adaptor, said outer needle proximal end portion, and said restricting plate are configured so that, when the downward pushing force is released, said restricting plate is pushed upwardly by said plate spring portion and said protrusion of said restricting plate engages one of said grooves on said outer needle proximal end portion so that said inner needle is in a locked state to prevent said inner needle from advancing or retracting relative to said outer needle.

2. The anesthetic compound needle according to claim 1, wherein said restricting plate has a finger contact portion on an upper portion thereof, said finger contact portion being bent in a horizontal direction.

3. The anesthetic compound needle according to claim 2, wherein said finger contact portion is on an opposite end of said restricting plate from said protrusion such that said finger contact portion is located at an upper outer surface of said outer needle proximal end portion and said protrusion is located at said lower outer surface of said outer needle proximal end portion.

4. The anesthetic compound needle according to claim 1, wherein said proximal end of said outer needle is directly connected to said outer needle proximal end portion.

5. The anesthetic compound needle according to claim 4, wherein said outer needle proximal end portion is directly connected to said adaptor.

6. The anesthetic compound needle according to claim 1, wherein said outer needle proximal end portion is directly connected to said adaptor.

* * * * *